United States Patent [19]
Blaney et al.

[11] Patent Number: 5,580,348
[45] Date of Patent: Dec. 3, 1996

[54] ABSORBENT STRUCTURE COMPRISING A MICROBIAL POLYSACCHARIDE AND A PROCESS OF MAKING THE SAME

[75] Inventors: Carol A. Blaney, Roswell; Joel Brostin, Alpharetta, both of Ga.; Theresa M. McIntire, Irvine, Calif.; Bernard J. Minerath, III, Oshkosh, Wis.

[73] Assignee: Kimberly-Clark Corporation, Neenan, Wis.

[21] Appl. No.: 241,117

[22] Filed: May 10, 1994

[51] Int. Cl.$^6$ ............... A61F 13/15; A61F 13/20
[52] U.S. Cl. ............ 604/367; 604/358; 604/374; 428/311.1; 428/311.5; 428/311.7; 428/315.5; 536/123.1
[58] Field of Search .................. 604/358, 364, 604/367–368, 372, 374; 428/311.5, 311.7, 315.5, 332; 536/123.1

[56] References Cited

U.S. PATENT DOCUMENTS

| | | |
|---|---|---|
| 4,378,431 | 3/1983 | Brown, Jr. . |
| 4,588,400 | 5/1986 | Ring et al. ............... 604/304 |
| 4,655,758 | 4/1987 | Ring et al. ............... 604/374 |
| 4,667,417 | 5/1987 | Graser et al. . |
| 4,704,116 | 11/1987 | Enloe . |
| 4,710,187 | 12/1987 | Boland et al. . |
| 4,742,164 | 5/1988 | Iguchi et al. . |
| 4,762,521 | 8/1988 | Roessler et al. . |
| 4,770,656 | 9/1988 | Proxmire et al. . |
| 4,798,603 | 1/1989 | Meyer et al. . |
| 4,873,218 | 10/1989 | Pekala . |
| 4,891,317 | 1/1990 | Brown, Jr. et al. . |
| 4,929,550 | 5/1990 | Byrom . |
| 4,942,128 | 7/1990 | Brown, Jr. . |
| 4,950,597 | 8/1990 | Saxena et al. . |
| 5,354,290 | 10/1994 | Gross ........................ 604/367 |

FOREIGN PATENT DOCUMENTS

| | | |
|---|---|---|
| 2169543A | 7/1986 | United Kingdom . |
| WO8911783 | 12/1989 | WIPO . |

OTHER PUBLICATIONS

Weatherwax, R. C. and Caulfield, D. F., "Cellulose Aerogel: An Improved Method for Preparing a Highly Expanded Form of Dry Cellulose", TAPPI, vol. 54, No. 6, Jun. 1971.

*Primary Examiner*—Mary Beth Jones
*Assistant Examiner*—P. Zuttarelli
*Attorney, Agent, or Firm*—Jeffrey B. Curtin

[57] ABSTRACT

Disclosed is an absorbent structure comprising a microbial polysaccharide having improved porosity and a process of making the same. The absorbent structure may be adapted for use in an absorbent product such as a diaper or incontinence product. The process involves the supercritical drying of a microbial polysaccharide to remove at least a portion of the aqueous medium in which the microbial polysaccharide is produced without unacceptably reducing the porosity of the microbial polysaccharide.

7 Claims, No Drawings

ABSORBENT STRUCTURE COMPRISING A MICROBIAL POLYSACCHARIDE AND A PROCESS OF MAKING THE SAME

BACKGROUND OF THE INVENTION

1. Field of the Invention

The present invention relates to an absorbent structure comprising a microbial polysaccharide and to the process of making the same. The invention more particularly concerns an absorbent structure comprising a microbial polysaccharide having an increased pore size and a reduced bulk density.

2. Description of the Related Art

Polysaccharides such as cellulose, starch and gums, are used for many purposes. For example, cellulose is used in the manufacture of absorbents, paper products, materials of construction, fillers for food products, wound dressings, filtration mediums and other products well known to those skilled in the art. Polysaccharides are synthesized not only by various plant systems, but also by microorganisms capable of forming polysaccharides as part of their life cycle. Polysaccharides produced by microorganisms are termed microbial polysaccharides and include a network of structural elements which are produced by the microorganisms. The microbial polysaccharide has pores which are defined by the spaces between the structural elements and may or may not be fibrous in nature. For example, some microbial polysaccharides, such as microbial cellulose, include a network of individual fibers and have pores which are defined by the spaces between the individual fibers. The fibers of such microbial polysaccharides are orders of magnitude finer than fibers of polysaccharides produced by plants. Microbial polysaccharides have a much greater surface area per unit volume compared to polysaccharides produced by plants. Such microbial polysaccharides are highly absorbent and very useful in the manufacture of many of the same products as more conventional polysaccharides produced by plants.

Synthesis of microbial polysaccharides generally occurs by inoculating a quantity of an aqueous culture medium containing the appropriate nutrients with a polysaccharide-producing microorganism and incubating the resulting culture under the proper conditions for a sufficient time to generate the microbial polysaccharide. The synthesis may occur in a static aerobic culture or a culture under agitation such as in a fermenter. The microbial polysaccharide produced in the culture medium generally exists in an aqueous medium. Such aqueous medium generally contains, in addition to water, nutrients, cells, cell debris, and other materials.

Many of the products, such as, for example, absorbent materials, that are manufactured from microbial polysaccharides require that at least a portion of the aqueous medium in which the microbial polysaccharides are produced be removed prior to use. The desired amount of the aqueous medium is removed to improve the absorbency and appearance of the microbial polysaccharides and the absorbent products manufactured from the microbial polysaccharides.

Many conventional methods for removing a portion of the aqueous medium from the microbial polysaccharide are known to those skilled in the art and include air-drying, oven-drying, solvent-drying, freeze-drying and the like. However, microbial polysaccharides produced by some of these conventional methods of removing the aqueous medium have pores, which are defined by the spaces between the structural elements of the microbial polysaccharide, which collapse due to the electrostrictive or surface tension forces resulting from the removal. The collapsed pores reduce the liquid transport and retention properties (absorbency) of the microbial polysaccharides. Thus, to maximize the absorbency of the microbial polysaccharide, it is desirable to maintain the open, fine pores of the microbial polysaccharide during the removal of at least a portion of the aqueous medium.

SUMMARY OF THE INVENTION

It is desirable to provide a natural-based absorbent material having absorptive properties similar to superabsorbent materials and, thus, suited for use in personal care absorbent products.

In one aspect, the present invention concerns an absorbent structure adapted for use in an absorbent product. The absorbent structure comprises a microbial polysaccharide having a mean pore size of at least about 0.01, desirably at least about 0.1, more desirably from about 0.1 to about 500 microns and even more desirably from about 0.1 to about 10 microns. The microbial polysaccharide also has a bulk density of from about 0.0001 to about 0.5 grams per cubic centimeter. The absorbent structure may further comprise a means for containing the microbial polysaccharide.

In another aspect, the present invention concerns an absorbent structure adapted for use in an absorbent product comprising a microbial polysaccharide which is produced by a process comprising the step of supercritical drying of the microbial polysaccharide. The supercritically-dried microbial polysaccharide has a mean pore size of at least about 0.01 microns, desirably from about 0.01 to about 500 microns and more desirably from about 0.1 to about 10 microns. The supercritically-dried microbial polysaccharide also has a bulk density of from about 0.0001 to about 0.5 grams per cubic centimeter.

The present invention further concerns a process for producing the microbial polysaccharide used in the manufacture of the absorbent structure. The process of the present invention comprises the supercritical drying of a microbial polysaccharide to remove at least a portion of the aqueous medium that is present when the microbial polysaccharide is produced.

The microbial polysaccharide resulting from this process is very porous and has a reduced bulk density. Such microbial polysaccharides may be used in the manufacture of absorbent structures which are biodegradable and used in absorbent articles such as wipes, tissues, diapers, training pants, feminine napkins, nursing pads, tampons, adult incontinence products, bandages, filtration mediums and the like.

DETAILED DESCRIPTION OF THE PREFERRED EMBODIMENT

As used herein, the term "microbial polysaccharide" refers to a carbohydrate structure developed from microorganisms and made up of one or more molecules of monosaccharides which comprise any of the class of simple sugars that contain in each molecule one or more alcoholic hydroxyl group and one carboxyl group of aldehyde or ketone character. The microbial polysaccharide has pores which are defined by the spaces between the network of structural elements produced by the microorganisms.

As used herein, the term "mean" refers to the overall weighted mean and is calculated according to the following formula:

$$\text{Overall Weighted Mean} = \frac{\sum_{i=1}^{K} n_i r_i}{\sum_{i=1}^{K} n_i}$$

wherein, i=the interval, $n_i$=the number of observations in the interval (i), and $r_i$=the average value of the test determinations for the observations in the interval (i).

As used herein, the term "average" indicates the average of 2 or more individual test determinations for a given sample.

As used herein, the term "pore size" is determined from the equivalent circular diameter of the pores of the microbial polysaccharides and may be expressed in units of distance, for example, inches or microns. The mean pore size of the microbial polysaccharides of the present invention is determined according to the above-referenced "Overall Weighted Mean" formula and as set forth below in connection with the examples.

As used herein, the term "bulk density" refers the weight of a material per unit of volume and is generally expressed in units of mass per unit bulk volume (e.g., grams per cubic centimeter). The average bulk density of the microbial polysaccharide of the present invention is determined as set forth below in connection with the examples.

As used herein, the term "absorbency" refers to the Free-Swell Capacity of a material. The Free-Swell Capacity is the capacity, in grams, of a material to absorb an aqueous, 0.9 weight percent saline solution over a period of time of 20 minutes. Free-Swell Capacity is reported in grams of saline solution absorbed in 20 minutes per gram of material being tested. Free-Swell Capacity is determined as set forth below in connection with the examples. The average absorbency of the microbial polysaccharide of the present invention is determined by the average of 2 or more individual absorbency (Free-Swell Capacity) determinations for a given sample.

As used herein, the term "continuous-flow pressure apparatus" refers to an apparatus comprising a vessel capable of maintaining an internal pressure wherein a liquid under pressure can be fed through an inlet valve into the vessel, maintained at an elevated pressure, and allowed to exit the vessel through an exit valve while maintaining a pressure within the vessel. This permits a continuous flow of a pressurized fluid through the vessel. In addition, prior to allowing the liquid to exit, the inlet and exit valve may be closed such that the pressure and temperature of the liquid may be varied to produce the desired result.

As used herein, the term "supercritical fluid" refers to a fluid held at a pressure and temperature above its critical point. The critical point is the highest pressure and temperature at which the fluid can co-exist as a gas and a liquid. For example, the critical pressure and temperature of carbon dioxide are 72.8 atmospheres and 31.1 degrees Centigrade, respectively. Carbon dioxide held at a pressure and temperature above its critical point is in a supercritical condition or state.

As used herein, the term "supercritical drying" refers to a process that uses one or more fluids, with at least one being under supercritical conditions part of the time, to displace and remove specific substances within a given matrix, mixture, dispersion, emulsion, suspension, solution or the like. While under supercritical conditions, the supercritical fluid is vented to atmospheric pressure at a temperature sufficiently high enough to prevent condensation of the fluid. It is often desirable that the pressure of the supercritical fluid be reduced over a period of time of from about 1 minute to about 120 minutes to prevent rapid cooling which causes condensation. The material produced by this process is relatively devoid of surface tension-induced shrinkage and collapse which occurs during conventional methods known to those skilled in the art for removing dispersed or continuous phases such as air-drying, oven-drying, solvent-drying, freeze-drying and the like. Many supercritical fluids such as, for example, supercritical carbon dioxide, may be used in the supercritical drying process. In addition, supercritical drying can be used with materials that have been exposed to solvent exchange or similar diffusion and/or convection controlled processes, provided that the final step is to vent the supercritical fluid to the atmosphere.

When using supercritical drying with the microbial polysaccharide of the present invention, the supercritical fluid should displace at least one constituent of the aqueous medium. The supercritical fluid may displace a portion of a constituent of the aqueous medium, a portion of several constituents of the aqueous medium, and/or a portion of the aqueous medium as a whole. It is generally desired that the supercritical fluid displaces a majority of the water constituent of the aqueous medium. If the microbial polysaccharide is first subjected to a solvent exchange, the supercritical fluid should be miscible with the solvent. The supercritical fluid may then displace at least a portion of the solvent. The displacement of at least a portion of the aqueous medium or the solvent may suitably occur in a continuous-flow pressure apparatus.

As used herein, the term "inoculum" refers to a suspension of polysaccharide-producing microorganisms.

Processes for producing microbial polysaccharides, such as microbial cellulose, are well-known to those skilled in the art. In general, the process comprises aerobically incubating a quantity of nutrient medium comprising a polysaccharide-producing microorganism. For example, such processes for producing microbial cellulose in a static aerobic medium are described in U.S. Pat. Nos. 4,378,431 issued Mar. 29, 1983, to Brown, Jr.; 4,588,400 issued May 13, 1986, to Ring et al.; and 4,742,164 issued May 3, 1988, to Iguchi et al., the disclosures of which are incorporated by reference. The microbial polysaccharide is generally formed on the surface of a static culture which is usually contained in shallow trays. In the alternative, microbial polysaccharides may be produced in a continuous cultivation process such as in a fermenter. Many well known processes are available for fermentations where fresh nutrient is continually added to the culture comprising the polysaccharide-producing microorganisms while depleted nutrient medium containing metabolic waste products and produced microbial polysaccharides are withdrawn. For example, such processes are described in U.S. Pat. No. 4,929,550 issued May 29, 1990, to Byrom; and British Patent No. 2 169 543 published July 16, 1986, to Roberts et al., the disclosures of which are incorporated by reference.

Any microorganism capable of producing a microbial polysaccharide is suitable for use in the present invention. Suitable polysaccharide-producing microorganisms include, for example, members of the Acetobacter, Rhizobium, Agrobacterium, Pseudomonas and Alcaligenes genera. Many varieties of polysaccharide-producing microorganisms, particularly the cellulose-producing Acetobacter pasteurianus, formerly classified as Acetobacter xylinum (Bergey's Manual of Systematic Bacteriology Vol. 1, pp. 268–274, (1984)), exist in natural surroundings such as, for example, damp forests. In one embodiment of the present invention, *Acetobacter pasteurianus* is the microorganism used to produce microbial cellulose.

The growth of such polysaccharide-producing microorganisms and the synthesis of microbial polysaccharides occurs generally in a nutrient medium. Any nutrient medium capable of sustaining the production of the microbial polysaccharide by the microorganisms is suitable for use in the present invention. A suitable nutrient medium comprises a water soluble carbon source such as, for example, sucrose, hexose or glucose. Suitable nutrient mediums such as, for example, Schramm & Hestrin medium (Biochem J. (58) pp. 345–52 (1954)), which generally contains about 20 grams per liter glucose, 5 grams per liter peptone, 5 grams per liter yeast extract, 2.7 grams per liter anhydrous dibasic sodium phosphate, and 1.15 grams per liter citric acid monohydrate, are well known to those skilled in the art. The pH of the nutrient medium is generally adjusted to from about 3.5 to about 7.0 with the addition of an acid such as hydrochloric acid or a base such as sodium hydroxide. Any temperature at which the production of the microbial polysaccharide by the microorganisms is sustained is believed suitable for the present invention. A suitable temperature for the production of microbial polysaccharides is from about 15 to about 40 degrees Centigrade. The total amount of time generally required for acceptable microbial polysaccharide production in a static nutrient medium is from about 1 to about 25 days.

Other substances such as, for example, polysaccharide derivatives, may be added to the nutrient medium to alter the microbial polysaccharide produced by the polysaccharide-producing microorganisms. Such polysaccharide derivatives alter the microbial polysaccharide by interfering with the formation processes to alter the order or arrangement of the structure of the microbial polysaccharide. Any polysaccharide derivative that produces the desired alterations in the microbial polysaccharide is suitable for addition to the nutrient medium. Such polysaccharide derivatives include, for example, cellulose, starch, or dextran having substituent groups such as, for example, alkyl, alkyl carboxy, alkyl hydroxy, sulfate, sulfonic acid or alkyl phosphate. A desirable polysaccharide derivative is carboxymethyl cellulose.

The microbial polysaccharide produced by the microorganisms generally includes a network of structural elements having pores which are defined by the spaces between the structural elements. The microbial polysaccharide generally exists in an aqueous medium. Such aqueous medium generally contains, in addition to water, nutrients, cells, cell debris and other materials. It is generally desired that at least a portion of the aqueous medium be removed from the microbial polysaccharide before it is employed in an absorbent structure. The removal of at least a portion of the aqueous medium improves the absorbency and appearance of the microbial polysaccharide. Many conventional methods for the removal of at least a portion of a dispersed or continuous phase, such as an aqueous medium or a solvent, are well known to those skilled in the art such as, for example, air-drying, oven-drying, solvent-drying, freeze-drying and the like. However, the pore size of microbial polysaccharides obtained by these conventional methods of removing dispersed or continuous phases is reduced because the pores of the microbial polysaccharide, which are defined by the spaces between the structural elements of the microbial polysaccharide, collapse due to the electrostrictive (surface tension) forces that result from the removal.

The present invention concerns an absorbent structure which may be used as a filter medium or may be adapted for use in absorbent products such as wipes, tissues, diapers, training pants, feminine napkins, nursing pads, adult incontinence products and the like. The absorbent structure comprises a microbial polysaccharide having a mean pore size of at least about 0.01 microns, desirably at least about 0.1 microns, more desirably from about 0.1 to about 500 microns, and even more desirably from about 0.1 to about 10 microns. In addition, the bulk density of the microbial polysaccharide of the present invention is from about 0.0001 to about 0.5 grams per cubic centimeter, desirably from about 0.001 to about 0.5, more desirably from about 0.005 to about 0.1 grams per cubic centimeter, and even more desirably from about 0.01 to about 0.05 grams per cubic centimeter. Further, the absorbency of the microbial polysaccharide is at least about 10 grams of aqueous saline solution (0.9 weight percent) per gram of polysaccharide, desirably from about 10 to about 100 grams of aqueous saline solution per gram of polysaccharide, and more desirably from about 20 to about 1000 grams of aqueous saline solution per gram of polysaccharide. In a specific aspect of the invention, the absorbent structure comprises a microbial polysaccharide which is microbial cellulose.

In another aspect, the absorbent structure of the present invention includes a microbial polysaccharide produced by the process of supercritical drying of the microbial polysaccharide. The supercritically-dried microbial polysaccharide has a mean pore size of at least about 0.01 microns, desirably from about 0.01 to about 500 microns and more desirably from about 0.1 to about 10 microns. The supercritically-dried microbial polysaccharide of the present invention also has a bulk density which is from about 0.0001 to about 0.5 grams per cubic centimeter, desirably from about 0.001 to about 0.5, more desirably from about 0.005 to about 0.1 grams per cubic centimeter, and even more desirably from about 0.01 to about 0.05 grams per cubic centimeter. Further, the absorbency of the supercritically-dried microbial polysaccharide is at least about 10 grams of aqueous saline solution (0.9 weight percent) per gram of polysaccharide. In a specific aspect, the absorbent structure of the present invention comprises a microbial cellulose produced by the process of supercritical drying of the microbial cellulose.

The process for producing the microbial polysaccharide of the present invention comprises supercritically drying the microbial polysaccharide. In one aspect, the microbial polysaccharide is subjected to supercritical fluid exchange wherein at least a portion of the aqueous medium in which the microbial polysaccharide is produced is displaced with a supercritical fluid. It is generally desired that the supercritical fluid displaces a majority of the water constituent of the aqueous medium. For example, the supercritical fluid may displace about 50 percent, desirably about 75 percent, and more desirably about 95 percent of the water constituent of the aqueous medium. It is, however, not necessary that the microbial polysaccharide be completely water free. Any supercritical fluid capable of displacing at least a portion of the aqueous medium is suitable for use in the present invention. Suitable supercritical fluids include, but are not limited to, carbon dioxide, nitrous oxide and freon.

The supercritical fluid exchange desirably occurs in a continuous-flow pressure apparatus where the pressure and temperature of the supercritical fluid may be maintained above the critical point. For example, the microbial polysaccharide which is immersed in the aqueous medium may be sealed inside a vessel of a continuous flow pressure apparatus. A second fluid may then be pumped through the apparatus until the desired amount of the aqueous medium is displaced. At this point, the microbial polysaccharide is immersed in the second fluid. The temperature and/or pressure of the second fluid may then be increased to a temperature and pressure above the critical temperature and pressure of the fluid thereby causing the second fluid to go into a supercritical condition or state.

The supercritical fluid-saturated microbial polysaccharide is then dried. Suitably, the supercritical fluid is vented to atmospheric pressure at a sufficiently high temperature to allow the supercritical fluid in the microbial polysaccharide to transform from a supercritical state to a vapor or gaseous phase without condensing. Desirably, the pressure is reduced over a period of time of from about 1 to about 120 minutes to prevent rapid cooling which would also cause condensation. If the fluid is allowed to condense, the porous structure and pores of the microbial polysaccharide may collapse due to the electrostrictive or surface tension forces that may result if the condensed fluid is removed. Thus, the above described process of using supercritical drying effectively removes at least a portion of the aqueous medium in which the microbial polysaccharide is produced without causing an unacceptable degree of pore collapse.

In an alternative embodiment, prior to supercritically drying the microbial polysaccharide, the microbial polysaccharide may be cleansed to remove at least a portion of the nutrients, cells, cell debris and other materials that may be present. The microbial polysaccharide may be cleansed by washing it with water, aqueous base solutions and other like substances. For example, the microbial polysaccharide may be cleansed with an aqueous solution of sodium hydroxide, e.g., about 0.5 molar.

In another alternative embodiment, at least a portion of the aqueous medium in which the microbial polysaccharide is produced is displaced with a solvent prior to supercritically drying the microbial polysaccharide. As used herein, "solvent" refers to a medium in which water is miscible. Any solvent capable of displacing at least a portion of the aqueous medium is suitable for use in the present invention. Desirably, the solvent used is miscible with water and the supercritical fluid. Suitable solvents for the solvent exchange include, for example, ethanol, methanol, acetone, isopropanol, mixtures thereof and the like. The solvent may displace a portion of a single constituent of the aqueous medium (e.g., water), a portion of several constituents of the aqueous medium, and/or a portion of the aqueous medium as a whole. For example, the solvent may displace about 50 percent, desirably about 75 percent, and more desirably about 95 percent of the water constituent of the aqueous medium.

The microbial polysaccharide may be "shock" treated with pure solvent or may be treated with successive rinses of solvent/water mixtures of increasing solvent concentrations to displace at least a portion of the aqueous medium prior to supercritical drying. Desirably, at least a portion of the aqueous medium in which the microbial polysaccharide is produced is displaced with successive rinses of solvent/water mixtures of increasing solvent concentration and then pure solvent. For example, the microbial polysaccharide may be treated with successive rinses of ethanol/water mixtures of increasing ethanol concentration, and then finally in pure ethanol (e.g., 20/80, 40/60, 60/40, 80/20, 100/0).

The solvent-saturated microbial polysaccharide is then supercritically dried wherein at least a portion of the solvent is removed without causing an unacceptable degree of pore structure collapse. The solvent present in the microbial polysaccharide is displaced with either a supercritical fluid or a fluid which is then caused to go into a supercritical condition. The supercritical fluid-saturated microbial polysaccharide is then dried as described above.

The mean pore size of the supercritically-dried microbial polysaccharide of the present invention is generally greater than the mean pore size of microbial polysaccharides wherein at least a portion of the aqueous medium is removed by conventional methods of removing dispersed or continuous phases. The supercritically-dried microbial polysaccharide desirably has a mean pore size which is at least about 50 percent greater and more desirably at least about 100 percent greater than the pore size of an identical microbial polysaccharide wherein at least a portion of the aqueous medium is removed by air-drying. In addition, the supercritically-dried microbial polysaccharide of the present invention desirably has a bulk density which is at least about 90 percent lower and more desirably at least about 95 percent lower than the bulk density of an identical microbial polysaccharide wherein at least a portion of the aqueous medium is removed by air-drying.

The novel process of using supercritical drying to remove at least a portion of the aqueous medium in which a microbial polysaccharide is produced provides an absorbent structure of microbial polysaccharide which can be adapted for use in many absorbent products. The increased pore size and lower bulk density of the microbial polysaccharide produced by the novel process of the present invention, relative to that realized when more conventional drying methods are used, enhances the liquid transport and retention properties of the microbial polysaccharide. Thus, microbial polysaccharides with an increased pore size and reduced bulk density have a higher absorbency. The microbial polysaccharides of the present invention may be used in absorbent articles such as diapers, training pants, adult incontinence products, feminine napkins and nursing pads among other uses. Moreover, the microbial polysaccharides of the present invention may be used independently as an absorbent material such as a tissue, wipe, bandage, or filtration medium.

Absorbent articles such as diapers, training pants, adult incontinence products and the like comprise a porous facing layer, an outer cover and an absorbent structure located between the facing layer and the outer cover. Specific embodiments of diapers and incontinence products are described, for example, in U.S. Pat. Nos. 4,704,116 issued Nov. 3, 1987, to Enloe; No. 4,798,603 issued Jan. 17, 1989, to Meyer et al.; No. 4,710,187 issued Dec. 1, 1987, to Boland et al.; No. 4,770,656 issued Sep. 13, 1988, to Proxmire et al.; and No. 4,762,521 issued Aug. 9, 1988, to Roessler et al.; the disclosures of which are incorporated by reference. The absorbent structure that is disposed between the porous facing layer and the outer cover may be the absorbent structure of the present invention. The absorbent structure may also comprise a means for containing the microbial polysaccharide. For example, the microbial polysaccharide may be contained by a nonwoven wrap sheet such as a sheet of tissue or of nonwoven fibers. Alternatively, the microbial polysaccharide may be incorporated into a fibrous matrix such as wood pulp fluff or extruded polymeric fibers. The microbial polysaccharide may also be adhered to a substrate or sandwiched between two substrates which are bound together at least in certain locations. Any means of containing the microbial polysaccharide in place are suited for use in the present invention. Alternatively, the microbial polysaccharide may be contained by the porous facing layer and the outer layer of the absorbent article.

While the invention has been described in detail with respect to specific embodiments thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and any equivalents thereto.

Test Methods

Pore Size Test

The Pore Size Test is a test which measures the mean pore size of the sample of material. The mean pore size is the overall weighted mean pore size of the samples and is calculated using the "Overall Weighted Mean" formula set forth above. The mean pore size is recorded in units of distance such as microns.

For the purposes of the present invention, a suitable technique for determining and measuring the effective mean pore size of the sample of material is by employing a scanning electron microscope, such as, for example, a JEOL 6400/JEOL 840 Scanning Electron Microscope distributed by JEOL, Inc. of Peabody, Mass. The pore size is measured at the surface of the sample. The surface measurements can be made with a scanning electron microscope employing standard techniques known to persons skilled in the art.

More particularly, a suitable technique involves randomly selecting test samples measuring approximately one-half inch by one inch, and then examining a major face surface of each sample. Conceptually, the major surface extends generally along the horizontal x-y plane. Employing conventional techniques, the selected major surface of each sample is coated with a heavy metal, such as gold, to prepare it for analysis with the electron microscope. Twelve, random photomicrographs are taken as a general rule to represent the sample. Such a selection of twelve, random photomicrographs provides adequate statistical stability and can be arranged to form a convenient photo montage for macrostage automation. The choice of magnification for the photomicrographs is not critical for orientation measurements, but a "1% rule" for fiber sizes ratioed to field width is used.

The photographs are placed on a macroviewer of an image-analysis system, such as a Quantimet 900 series image analysis system distributed by Leica Instruments, Inc. of Deerfield, Illinois. Detection (threshholding) is set for the extraction of black pores from amidst the white fiber matrix, and the equipment is programmed in a conventional manner to generate a feature-specific histogram based upon the equivalent circular diameter (ECD). The ECD is defined as the diameter of a circle which has substantially the same area as the "pore" space bounded by three or more fibers. At least several hundred pores, and up to several thousand pores, are then measured and analyzed with all of the individual pore ECD's accumulated into the histogram. Data values produced during the analysis can include the mean, the standard deviation, and selected percent entries in the low-end and high-end regions of the histogram. The mean pore size of each sample is then recorded.

Bulk Density Test

Bulk Density is calculated according to the following formula: density(g/cc or grams per cubic centimeter)= sample weight(grams)/sample bulk volume[(cubic centimeters)=area (cm$^2$)×thickness (cm)]. The weight, area and thickness of the absorbent sample are measured. The Bulk Density of the absorbent sample is then calculated using the above mentioned formula. The average bulk density is the average of two or more bulk density determinations for the given sample.

Free-Swell Capacity Test

The Free-Swell Capacity is a test which measures the ability of an absorbent material to absorb a liquid (0.9 weight percent solution of sodium chloride in distilled water). The Free-Swell Capacity is reported as the weight of the saline solution absorbed after 20 minutes, expressed as grams of saline absorbed per gram of absorbent.

The apparatus and method for determining Free-Swell Capacity will be described. The apparatus includes a laboratory jack having an adjustable knob for raising and lowering a platform. A laboratory stand supports a spring which is connected to a modified thickness meter probe. The meter probe passes through the housing of a meter which is rigidly supported by the laboratory stand. A plastic sample cup, which contains the absorbent material sample to be tested, has a liquid-permeable bottom and rests within a Petri dish, which contains the saline solution to be absorbed. A spacer disc rests on top of the sample.

The sample cup consists of a plastic cylinder having a 1 inch inside diameter and an outside diameter of 1.25 inch. The bottom of the sample cup is formed by adhering a 300 micron mesh metal screen to the end of the cylinder by heating the screen above the melting point of the plastic and pressing the plastic cylinder against the hot screen to melt the plastic and bond the screen to the plastic cylinder.

The modified thickness meter used to measure the expansion of the sample while absorbing the saline solution is a Mitutoyo Digimatic Indicator, IDC Series 543, Model 543-180, having a range of 0–0.5 inch and an accuracy of 0.00005 inch (Mitutoyo Corporation, 31-19, Shiba 5-chome, Minato-ku, Tokyo 108, Japan). As supplied from Mitutoyo Corporation, the thickness meter contains a spring attached to the probe within the meter housing. This spring is removed to provide a free falling probe, which has a downward force of about 27 grams. In addition, the cap over the top of the probe located on the top of the meter housing is also removed to enable attachment of the probe to a suspension spring (available from McMaster-Carr Supply Co., Chicago, Ill., Item No. 9640K41), which serves to counter or reduce the downward force of the probe to about 1 gram, ±0.5 gram. A wire hook can be glued to the top of the probe for attachment to the suspension spring. The bottom tip of the probe is also provided with an extension needle (Mitutoyo Corporation, Part No. 131279) to enable the probe to be inserted into the sample cup.

To carry out the test, a sample of the absorbent material is placed into the sample cup. The sample is then covered with a plastic spacer disc, weighing 4.4 grams, which is slightly smaller than the inside diameter of the sample cup and serves to protect the sample from being disturbed during the test. The sample cup is placed in the Petri dish on the platform of the laboratory jack raised up until it contacts the tip of the probe. The meter is zeroed. A sufficient amount of saline solution is added to the Petri dish (50–100 milliliters) to begin the test. The distance the spacer disc is raised by the expanding sample as it absorbs the saline solution is measured by the probe. This distance, multiplied by the cross-sectional area inside the sample cup, is a measure of the expansion volume of the sample due to absorption. Factoring in the density of the saline solution and the weight of the sample, the amount of saline solution absorbed is readily calculated. The weight of saline solution absorbed after 20 minutes is the Free-Swell Capacity value, expressed as grams saline solution absorbed per gram of absorbent. If desired, the readings of the modified thickness meter can be continuously input to a computer (Mitutoyo Digimatic Mini-processor DP-2 DX) to make the calculations and provide Free-Swell Capacity readings. As a cross-check, the Free-Swell Capacity can also be determined by determining the weight difference between the sample cup before and after the test, the weight difference being the amount of solution absorbed by the sample. The average absorbency is the average of two or more of the Free-Swell Capacity determinations of the samples.

EXAMPLES

Example 1

A Schramm & Hestrin medium comprising about 80 grams glucose, 20 grams peptone, 20 grams yeast extract, 10.8 grams anhydrous dibasic sodium phosphate ($Na_2HPO_4$), 4.2 grams citric acid monohydrate, and 4 liters of distilled water is prepared by mixing. The pH of the medium is then adjusted to 4.8 by the addition of an amount of a 5.0M aqueous solution of hydrochloric acid. The medium is then autoclaved for 20 minutes at a temperature of 121 degrees Centigrade and a pressure of 15 pounds per square inch and allowed to cool.

Thirty-eight sterilized Petri plates having the dimensions of 150 millimeters×25 millimeters are used to contain the medium. 100 milliliters of the Schramm & Hestrin medium is placed in each Petri plate. The depth of the medium in the plates is approximately 0.65 centimeters.

The Petri plates are then inoculated with a strain of *Acetobacter pasteurianus*, ATCC no. 10821 from the American Type Culture Collection (ATCC), Rockville, Md. Each Petri plate is inoculated with 1 milliliter of an inoculum of ATCC no. 10821 at a concentration of $3\times10^7$ CFU per milliliter (Colony Forming Units per milliliter). The plates are then placed in an incubator at a temperature of 28 degrees Centigrade.

After 13 days of incubation the microbial cellulose is harvested. The aqueous medium in which the samples of microbial cellulose are produced is then removed by the following process. The microbial cellulose samples are placed in two 2 liter beakers and washed several times in an excess of distilled water. The samples are allowed to stand in an excess of a 0.5M aqueous solution of sodium hydroxide for approximately 72 hours. The sodium hydroxide solution is then decanted and the microbial cellulose samples are each washed three times with an excess of distilled water at approximately 12 hour intervals. The samples are then covered with an excess of distilled water and the pH is adjusted to approximately 3.0 by the addition of a 5.0 M aqueous solution of hydrochloric acid. The beakers containing the samples are allowed to stand for approximately 24 hours. The samples are then washed three more times with an excess of distilled water at approximately 12 hour intervals.

The samples are then subjected to successive rinses of ethanol/water mixtures of increasing ethanol concentration, and then with pure ethanol. The microbial cellulose samples are rinsed in an excess of ethanol/water mixtures containing 20 volume percent ethanol, 40 volume percent ethanol, 60 volume percent ethanol and 80 volume percent ethanol. The samples are allowed to stand in each ethanol/water mixture for approximately one hour before being rinsed in the next ethanol/water mixture of increased ethanol concentration. The samples are then rinsed in an excess of pure ethanol three times at approximately one hour intervals.

The samples are then subjected to supercritical drying by the following process. The samples are placed in a vessel of a continuous-flow pressure apparatus, and supercritical carbon dioxide at a pressure of about 1400 pounds per square inch (100 atmospheres) and a temperature of about 45 degrees Centigrade is flowed through the samples for approximately one hour. The vessel is then sealed to stop the flow of supercritical carbon dioxide and the pressure within the vessel is slowly released to the atmosphere over a period of approximately one hour while holding the temperature constant. The vessel is then opened and the microbial cellulose samples are removed.

The samples of microbial cellulose are then subjected to the Free-Swell Capacity test (absorbency) and the pore size test as described above. The average absorbency of the samples is 89.15 grams of saline per gram of microbial cellulose. The samples also have a mean pore size of 0.167 microns.

Example 2

A Schramm & Hestrin medium comprising about 20 grams glucose, 5 grams peptone, 5 grams yeast extract, 2.7 grams anhydrous dibasic sodium phosphate ($Na_2HPO_4$), 1.05 grams citric acid monohydrate, and 1 liter of distilled water is prepared by mixing. In addition, 10 grams of carboxymethyl cellulose (CMC) obtained from the Aqualon Company of Hopewell, Virginia, under product no. CMC-12M8P is added to the medium. The medium is heated to dissolve the CMC. The pH of the medium is adjusted to 4.8 by the addition of an amount of a 5.0 M aqueous solution of hydrochloric acid. The medium is then autoclaved for 20 minutes at a temperature of 121 degrees Centigrade and a pressure of 15 pounds per square inch and allowed to cool.

Nine sterilized Petri plates having the dimensions of 150 millimeters×25 millimeters are used to contain the medium. 100 milliliters of the Schramm & Hestrin medium with CMC is placed in each Petri plate. The depth of the medium in the plates is approximately 0.65 centimeters.

The Petri plates are then inoculated with a strain of *Acetobacter pasteurianus*, ATCC no. 53582 (on deposit from U.S. Pat. No. 4,942,128) from the American Type Culture Collection (ATCC), Rockville, Md. Each Petri plate is inoculated with 1 milliliter of an inoculum of ATCC no. 53582 at a concentration of $4.5\times10^7$ CFU per milliliter. The plates are then placed in an incubator at a temperature of 28 degrees Centigrade.

After 5 days of incubation the microbial cellulose is harvested. The aqueous medium in which the samples of microbial cellulose are produced is then removed by the following process. The microbial cellulose samples are placed in two 2 liter beakers and washed several times in an excess of distilled water. The samples are allowed to stand in an excess of a 0.5M aqueous solution of sodium hydroxide for approximately 72 hours. The sodium hydroxide solution is then decanted and the microbial cellulose samples are washed three times with an excess of distilled water at approximately 12 hour intervals. The samples are then covered with an excess of distilled water and the pH is adjusted to approximately 3.0 by the addition of a 5.0M aqueous solution of hydrochloric acid. The beakers containing the samples are allowed to stand for approximately 24 hours. The samples are then washed three more times with an excess of distilled water at approximately 12 hour intervals.

The samples are then subjected to successive rinses with ethanol/water mixtures of increasing ethanol concentration, and then with pure ethanol. The microbial cellulose samples are rinsed in an excess of ethanol/water mixtures containing 20 volume percent ethanol, 40 volume percent ethanol, 60 volume percent ethanol and 80 volume percent ethanol. The samples are allowed to stand in each ethanol/water mixture for approximately one hour before being rinsed in the next ethanol/water mixture of increased ethanol concentration. The samples are then rinsed in an excess of pure ethanol three times at approximately one hour intervals.

The samples are then subjected to supercritical drying by the following process. The samples are placed in a vessel of a continuous-flow pressure apparatus, and supercritical carbon dioxide at a pressure of about 1400 pounds per square inch (100 atmospheres) and temperature of about 45 degrees Centigrade is flowed through the samples for approximately one hour. The vessel is then sealed to stop the flow of supercritical carbon dioxide, and the pressure is slowly released to the atmosphere over a period of approximately one hour while holding the temperature constant. The vessel is then opened and the samples of microbial cellulose are removed.

The samples of microbial cellulose are then subjected to the Free-Swell Capacity test (absorbency) and the pore size test as described above. The average absorbency of the samples is 42.34 grams of saline per gram of microbial cellulose. The samples also have a mean pore size of 0.188 microns.

Example 3

A Schramm & Hestrin medium comprising about 80 grams glucose, 20 grams peptone, 20 grams yeast extract, 10.8 grams anhydrous dibasic sodium phosphate ($Na_2HPO_4$), 4.2 grams citric acid monohydrate, and 4 liters of distilled water is prepared by mixing. The pH of the medium is adjusted to 4.8 by the addition of an amount of a 5.0M aqueous solution of hydrochloric acid. The medium is then autoclaved for 20 minutes at a temperature of 121 degrees Centigrade and a pressure of 15 pounds per square inch and allowed to cool.

Ten sterilized Petri plates having the dimensions of 150 millimeters×25 millimeters and twenty-four Petri plates having the dimensions of 150 millimeters×20 millimeters are used to contain the medium. 100 milliliters of the Schramm & Hestrin medium is placed in each Petri plate. The depth of the medium in the plates is approximately 0.65 centimeters.

The Petri plates are then inoculated with a strain of *Acetobacter pasteurianus*, ATCC no. 53582 (on deposit from U.S. Pat. No. 4,942,128) from the American Type Culture Collection (ATCC), Rockville, Md. The Petri plates are inoculated with 1 milliliter of an inoculum of ATCC no. 53582 at a concentration of $3.1 \times 10^6$ CFU per milliliter. The plates are then placed in an incubator at a temperature of 28 degrees Centigrade.

After 5 days of incubation the microbial cellulose is harvested. The aqueous medium in which the samples of microbial cellulose are produced is then removed by the following process. The microbial cellulose samples are placed in two 2 liter beakers and washed several times in an excess of distilled water. The samples are allowed to stand in an excess of a 0.5M aqueous solution of sodium hydroxide for approximately 24 hours. The sodium hydroxide solution is then decanted and the microbial cellulose samples are washed three times with an excess of distilled water at approximately 12 hour intervals. The samples are then covered with an excess of distilled water and the pH is adjusted to approximately 3.0 by the addition of a 5.0M aqueous solution of hydrochloric acid. The beakers containing the samples are allowed to stand for approximately 24 hours. The samples are then washed three more times with an excess of distilled water at approximately 12 hour intervals.

The samples are then subjected to successive rinses of ethanol/water mixtures of increasing ethanol concentration, and then with pure ethanol. The microbial cellulose samples are rinsed in an excess of ethanol/water mixtures containing 20 volume percent ethanol, 40 volume percent ethanol, 60 volume percent ethanol and 80 volume percent ethanol. The samples are allowed to stand in each ethanol/water mixture for approximately one hour before being rinsed in the next ethanol/water mixture of increased ethanol concentration. The samples are then rinsed in an excess of pure ethanol three times at approximately one hour intervals.

The samples are then subjected to supercritical drying by the following process. The samples are placed in a vessel of a continuous-flow pressure apparatus having a volume of 3 cubic centimeters and supercritical carbon dioxide at a pressure of about 1400 pounds per square inch (100 atmospheres) and temperature of about 45 degrees Centigrade is flowed through the samples for approximately one hour. The vessel is then sealed to stop the flow of supercritical carbon dioxide and the pressure in the vessel is slowly released to the atmosphere over a period of approximately one hour while holding the temperature constant. The vessel is then opened and the samples of microbial cellulose are removed.

The samples of microbial cellulose are then subjected to the Free-Swell Capacity test (absorbency), the pore size test, and the bulk density test as described above. The average absorbency of the samples is 74.83 grams of saline per gram of microbial cellulose. The samples have a mean pore size of 0.187 microns and an average bulk density of 0.023 grams of microbial cellulose per cubic centimeter. The samples also hold an average of 80 grams of tap water per gram of microbial cellulose.

Example 4

A first Schramm & Hestrin medium comprising about 40 grams glucose, 10 grams peptone, 10 grams yeast extract, 5.4 grams anhydrous dibasic sodium phosphate ($Na_2HPO_4$), 2.1 grams citric acid monohydrate, and 2 liters of distilled water is prepared by mixing. In addition, a second medium is prepared by mixing. The second medium is identical to the first except 20 grams of carboxymethyl cellulose (CMC) obtained from the Aqualon Company of Hopewell, Va., under product no. CMC-12M8P is added. The second medium is heated to dissolve the CMC. The pH of both mediums is then adjusted to 4.8 by the addition of an amount of a 5.0M aqueous solution of hydrochloric acid. Both mediums are then autoclaved for 20 minutes at a temperature of 121 degrees Centigrade and a pressure of 15 pounds per square inch and allowed to cool.

Two sterilized Petri plates having the dimensions of 150 millimeters×25 millimeters are used to contain the medium. 200 milliliters of the first medium is placed in one of the Petri plates. 200 milliliters of the second medium is placed in the other Petri plate. The depth of the medium in the plates is approximately 1.3 centimeters.

The Petri plates are then inoculated with a strain of *Acetobacter pasteurianus*, ATCC no. 10821 from the American Type Culture Collection (ATCC), Rockville, Md. Both Petri plates are inoculated with 1 milliliter of an inoculum of ATCC no. 10821 at a concentration of $3 \times 10^8$ CFU/ml. The plates are then placed in an incubator at a temperature of 28 degrees Centigrade.

After 16 days of incubation the microbial cellulose is harvested. The aqueous medium in which the samples of microbial cellulose are produced is then removed by the following process. The microbial cellulose samples are washed several times in an excess of distilled water and placed in individual 500 milliliter fleakers. 200 milliliters of a 0.5 M aqueous solution of sodium hydroxide is added to each fleaker. The fleakers are allowed to stand for approximately 12 hours. The sodium hydroxide solution is then decanted and the microbial cellulose samples are washed three times with an excess of distilled water. 250 milliliters of distilled water is then placed in each fleaker with the samples and the pH is adjusted to approximately 3.0 by the addition of a 5.0M aqueous solution of hydrochloric acid. The fleakers containing the samples are allowed to stand for approximately 3 hours. The microbial cellulose samples are washed five more times with an excess of distilled water.

The samples are then subjected to successive rinses of acetone/water mixtures of increasing acetone concentration, and then with pure acetone. The microbial cellulose samples are rinsed in an excess of acetone/water mixtures containing 20 volume percent acetone, 50 volume percent acetone, and 80 volume percent acetone. The samples are allowed to stand in each concentration for approximately one hour before being decanted and rinsed in the next concentration. The samples are then rinsed in an excess of pure acetone three times at approximately 15 minute intervals.

The samples are then individually subjected to supercritical drying by the following process. The samples are placed in the vessel of a continuous-flow pressure apparatus having a volume of approximately 28 cubic centimeters, an exit valve and an inlet valve. Liquid carbon dioxide at a pressure of about 955 pounds per square inch (65 atmospheres) and a temperature of about 25 degrees Centigrade is flowed through the samples for approximately 30 minutes to displace at least a portion of the ethanol. The vessel of the continuous flow pressure apparatus is then sealed by closing the inlet and exit valve and the pressure inside the chamber is raised to 1600 pounds per square inch (110 atmospheres) by heating the apparatus to a temperature above the critical temperature of carbon dioxide. The pressure is then slowly released to the atmosphere over a period of approximately one hour while holding the temperature constant. The samples of microbial cellulose are then removed from the vessel.

The samples of microbial cellulose are then subjected to the Free-Swell Capacity test (absorbency) as described above. The average absorbency of the samples of 10821 without CMC is 77.5 grams of saline per gram of microbial cellulose. The average absorbency of the samples of 10821 with CMC is 38.4 grams of saline per gram of microbial cellulose.

Example 5

Samples of microbial cellulose produced by *Acetobacter pasteurianus*, ATCC no. 10821 are prepared as set forth in Example 4 (both in the presence and absence of CMC in the nutrient medium). However, the samples are "shock" treated with an excess of pure ethanol as opposed to being treated with successive rinses of ethanol/water mixtures of increasing concentrations prior to being treated in pure ethanol. The samples are then subjected to supercritical drying by the process set forth in Example 4.

The samples of microbial cellulose are then subjected to the Free-Swell Capacity test (absorbency) as described above. The average absorbency of the samples without CMC is 34.1 grams of saline per gram of microbial cellulose. The average absorbency of the samples with CMC is 25.4 grams of saline per gram of microbial cellulose.

Comparative Example 1

Samples of microbial cellulose produced by *Acetobacter pasteurianus*, ATCC no. 53582 (on deposit from U.S. Pat. No. 4,942,128) from the American Type Culture Collection (ATCC), Rockville, Md., are prepared as set forth in Example 3. However, the samples are not subjected to supercritical drying. Instead, the samples are allowed to air-dry by letting the ethanol-soaked samples evaporate at ambient conditions.

The samples of air-dryed microbial cellulose are then subjected to the pore size test and the bulk density test as described above. The air-dryed samples have a mean pore size of 0.098 microns and an average bulk density of 0.65 grams of microbial cellulose per cubic centimeter. The air-dryed samples also hold 4.0 grams of tap water per gram of microbial cellulose.

Comparative Example 2

A first Schramm & Hestrin medium comprising about 25 grams glucose, 6.25 grams peptone, 6.25 grams yeast extract, 3.38 grams anhydrous dibasic sodium phosphate ($Na_2HPO_4$), 1.44 grams citric acid monohydrate, and 1.25 liters of distilled water is prepared by mixing. In addition, a second medium is prepared by mixing. The second medium is identical to the first except 12.5 grams of carboxymethyl cellulose (CMC) obtained from the Aqualon Company of Hopewell, Va., under product no. CMC-7MF is added. The second medium is heated to dissolve the CMC. The pH of both mediums is then adjusted to 4.8 by the addition of an amount of a 5.0M aqueous solution of hydrochloric acid. Both mediums are then autoclaved for 20 minutes at a temperature of 121 degrees Centigrade and a pressure of 15 pounds per square inch and allowed to cool.

Eight sterilized Petri plates having the dimensions of 150 millimeters×25 millimeters are used to contain the medium. 200 milliliters of the first medium is placed in four of the Petri plates. 200 milliliters of the second medium is placed in the other four Petri plates. The depth of the medium in all of the plates is approximately 1.3 centimeters.

The Petri plates are then inoculated with two strains of *Acetobacter pasteurianus*, ATCC no. 10821 and ATCC no. 23769 from the American Type Culture Collection (ATCC), Rockville, Md. Four Petri plates, two containing the first medium and two containing the second medium, are inoculated with 4 milliliters of an inoculum of ATCC no. 10821. The other four Petri plates are inoculated with 4 milliliters of an inoculum of ATCC no. 23769. The plates are then placed in an incubator at a temperature of 28 degrees Centigrade.

After 18 days of incubation the microbial cellulose is harvested. The microbial cellulose samples are placed in individual 500 milliliter fleakers. 200 milliliters of a 0.5M aqueous solution of sodium hydroxide is added to each fleaker. The fleakers are placed in a water bath at a temperature of 28 degrees Centigrade and shaken in an orbital fashion at 100 revolutions per minute for approximately 12 hours. The sodium hydroxide solution is then decanted and the microbial cellulose samples are washed three times with an excess of distilled water. 250 milliliters of distilled water is then placed in each fleaker with the samples and the pH is adjusted to approximately 3.0 by the addition of a 5.0 M aqueous solution of hydrochloric acid. The fleakers containing the samples are returned to the water bath at a temperature of 28 degrees Centigrade and shaken in an orbital fashion at 100 revolutions per minute for approximately 12 hours.

The microbial cellulose samples are washed five more times with an excess of distilled water. The fleakers containing the samples in an excess of distilled water are returned to the water bath at a temperature of 28 degrees Centigrade and shaken in an orbital fashion at 100 revolutions per minute for approximately 5 days. The samples are then washed with an excess of reagent grade distilled water and the water is decanted. 400 milliliters of reagent grade distilled water is then added to the fleakers containing the microbial cellulose samples. The fleakers containing the samples are returned to the water bath at a temperature of 28 degrees Centigrade and shaken in an orbital fashion at 100 revolutions per minute for approximately 2 days. The reagent grade distilled water is decanted and 350 milliliters of methanol is added to each fleaker. The fleakers are allowed to stand for approximately 4 days. The methanol is then decanted and replaced with 350 milliliters of fresh methanol. After two more days, the microbial cellulose samples are removed from the methanol and placed on watch glasses.

The microbial cellulose samples on the watch glasses are allowed to air dry for several hours. The samples are then placed in an oven at a temperature of approximately 95 degrees Centigrade for approximately 12 hours. The samples are then scraped from the watch glasses and weighed. Yields of between 6 and 22 milligrams (oven dry weight) of microbial cellulose resulted.

The samples of microbial cellulose are then subjected to the Free-Swell Capacity test (absorbency), the pore size test, and the bulk density test as described above. The average absorbency of samples without CMC is 11.18 grams of saline per gram of microbial cellulose. In addition, the average absorbency of samples with CMC is 14.12 grams of saline per gram of microbial cellulose.

What is claimed is:

1. An absorbent structure adapted for use in an absorbent product, said absorbent structure comprising a microbial polysaccharide network of structural elements having a mean pore size of from about 0.1 to about 10 microns.

2. The absorbent structure of claim 1 wherein said microbial polysaccharide has a bulk density of from about 0.0001 to about 0.5 grams per cubic centimeter.

3. The absorbent structure of claim 1 wherein said microbial polysaccharide has an absorbency of at least about 10 grams of an aqueous saline solution (0.9 weight percent) per gram of polysaccharide.

4. The absorbent structure of claim 1 wherein said absorbent structure further comprises a means for containing said microbial polysaccharide.

5. An absorbent article comprising a porous facing layer, a fluid impervious backing sheet and the absorbent structure of claim 1 disposed therebetween.

6. An absorbent structure adapted for use in an absorbent product, said absorbent structure comprising a microbial cellulose having a mean pore size of from about 0.1 to about 10 microns, a bulk density of from about 0.0001 to about 0.5 grams per cubic centimeter, and an absorbency of at least about 10 grams of an aqueous saline solution (0.9 weight percent) per gram of cellulose.

7. The absorbent structure of claim 6 wherein said absorbent structure further comprises a means for containing said microbial cellulose.

* * * * *